United States Patent
Mashiko et al.

(10) Patent No.: US 6,191,336 B1
(45) Date of Patent: Feb. 20, 2001

(54) METHOD OF HEAT-SEALING ADHESIVE BANDAGE AND ADHESIVE BANDAGE MADE BY USING SAID METHOD

(76) Inventors: Yasushi Mashiko, 637, Koyo-machi; Takeshi Yoshida, 39, Aza Ushiroda, Nishikawa; Toshikazu Saito, 74-3, Aza Ikenishita, Ohaza Nishikawa, all of Sukagawa-shi, Fukushima-ken, 962 (JP)

( * ) Notice: Under 35 U.S.C. 154(b), the term of this patent shall be extended for 0 days.

(21) Appl. No.: 09/263,703

(22) Filed: Mar. 5, 1999

Related U.S. Application Data

(63) Continuation of application No. 08/857,013, filed on May 15, 1997, now Pat. No. 5,928,972.

(30) Foreign Application Priority Data

May 17, 1996 (JP) .................................................... 8-146445

(51) Int. Cl.[7] .................................................... A61F 13/00
(52) U.S. Cl. ................................. 602/54; 602/41; 602/42
(58) Field of Search ............................... 602/41–59, 900, 602/904; 604/358, 365, 370, 372, 373, 378, 380, 383; 128/888, 889; 428/41, 102, 109, 195, 200, 317.5

(56) References Cited

U.S. PATENT DOCUMENTS 5,695,376 * 12/1997 Datta et al. ............................ 442/334
5,928,972 * 7/1999 Mashiko et al. ...................... 442/334

* cited by examiner

*Primary Examiner*—Kim M. Lewis

(57) ABSTRACT

Adhesive-coated sheet material having a base sheet with a layer of adhesive applied thereto. The base sheet comprises a laminate of a thermoplastic fiber fabric and a film of polymeric material, with at least a portion of the laminate being heat-sealed in a discontinuous pattern. The adhesive is applied to the fabric surface of the laminate. Methods of forming the adhesive-coated sheet are disclosed. A wound contacting pad may be adhered to the adhesive-coated sheet material to form an adhesive bandage.

20 Claims, 2 Drawing Sheets

METHOD OF HEAT-SEALING ADHESIVE BANDAGE AND ADHESIVE BANDAGE MADE BY USING SAID METHOD

This is a continuation of Application Ser. No. 08/857,013, filed May 15, 1997, now U.S. Pat. No. 5,928,972.

TECHNICAL FIELD OF THE INVENTION

This invention relates to adhesive-coated sheet materials, adhesive bandages comprising said adhesive-coated sheet materials, methods for making said sheet materials and methods for making said adhesive bandages. More specifically, the adhesive-coated sheet materials of the invention comprise fabric-film laminates which have been heat sealed in a discontinuous pattern and have had adhesive applied thereto. Even more specifically, the mentioned heat sealing is limited to regions of the sheet material adjacent its periphery. Preferably, the film is water vapor permeable and the fabric is porous so as to permit the relatively unimpeded passage of air and water vapor therethrough. Adhesive bandages according to the invention have improved adhesion to skin.

PRIOR ART

Methods of making vent holes in adhesive bandages in order to allow skin respiration when the adhesive bandages are applied to the skin are well-known. However, skin respiration is reduced in those portions of the bandages which do not have vent holes. Furthermore, such bandages permit an invasion of water through the vent holes, making it difficult for bandage users to conduct daily works such as kitchen work, a bath, etc. while adhering adhesive bandage after it has been contacted by water. Consequently in such cases, users must peel off the adhesive bandage when starting their daily work, and after the work is over a new bandage is applied again. This is laborious and may involve the disposal of still usable bandages. As a measure against these problems, an adhesive bandage comprising a base sheet made of a nonwoven fabric on which a film having water vapor permeability and water proofing property is laminated and an adhesive layer with water vapor permeability has been proposed.

In such an adhesive bandage, water invasion through the surface of the base sheet to a pad covering a wound may be prevented, but water will soak into the pad through a cut section of the nonwoven fiber fabric at the periphery of the bandage. Consequently it is necessary to prevent effectively the water soaking into the pad from the periphery of the bandage. As a measure against this problem, a method of sealing the periphery of the bandage by heating has been proposed in Japanese Laid-open Patent Hei 8-33673. However, even in bandages made by using such method, there is a problem in that the film may peel off the nonwoven fabric.

This invention uses an improved method of heat sealing in order to reduce or eliminate the aforementioned problems. As mentioned above, adhesive bandages in accordance with the invention have improved adhesion to skin.

DETAILED DESCRIPTION OF THE INVENTION

This invention relates to a method of heat sealing an adhesive bandage comprising a base sheet made by laminating a film on a thermoplastic fiber fabric and an adhesive layer set on a surface of the thermoplastic fiber fabric of said base sheet, characterized by said adhesive bandage being pattern-sealed, and more particularly, to a method of heat seal performed under the condition that the film does not melt and preferably only the thermoplastic fiber fabric melts. In the present invention, it is preferred that only the periphery of the adhesive bandage is pattern-sealed. Further it is preferred that the adhesive bandage is a dressing for medical treatment or an adhesive bandage having a pad. More particularly, the present invention relates to a method of heat-sealing an adhesive bandage which comprises laminating a base fabric made of a thermoplastic fiber having gas permeability on a film having water vapor permeability and gas permeability to make a base sheet, and coating an adhesive layer on the surface of the thermoplastic fiber fabric of the base sheet, characterized in that the pattern seal provides said bandage with water proofing property, and it is preferred that the heat seal is performed under the condition that the film does not melt but the thermoplastic fiber fabric melts, in particular, only the periphery of the adhesive bandage is sealed. Further it is preferable that the adhesive bandage has a pad. The present invention further relates to an adhesive bandage which being made by means of the methods described above, particularly an adhesive bandage having a pad which is made by means of the methods described above.

Adhesive bandage refers to a strip of a fabric or the other materials coated uniformly with a pressure-sensitive adhesive on one side of the surface, but an adhesive bandage in the present invention also includes an adhesive bandage having a wound-contacting pad and, further, a dressing for medical treatment to bind up a wound in wide range.

The thermoplastic fiber fabric used in the present invention includes woven fabrics and nonwoven fabrics made of thermoplastic elastomers. The reason the fiber fabric must be made of a thermoplastic elastomer is that the fiber fabric must melt and be pressed by pressure and heat to give the bandage a water-proofing property when heat-sealed. Also such fiber fabric preferably has gas permeability and elasticity.

The thermoplastic elastomer can be, for example, polystyrene type elastomers such as styrene-isoprene-styrene type block copolymer and hydrogenated block copolymers made by hydrogenating said block copolymer, polyurethanes, polyesters, polyolefines such as polyethylene, and mixtures thereof; they are, however, not critical. The fabric of the present invention can be either a woven fabric or a nonwoven fabric, but the nonwoven fabric is preferred because the directional dependency of physical properties such as elasticity is low.

When using a nonwoven fabric as a fiber fabric, the percentage expansion of the nonwoven fabric is preferably 100% or more, and the recovery at 50% expansion is 70% or more.

The weight of the nonwoven fabric of this invention has to be properly selected depending on properties of the nonwoven fabric itself, the laminating film and the adhesive, but cannot particularly be limited. However, the weight is preferably 20 to 200 g/M$^2$, more preferably 30 to 100 g/M$^2$. A thickness of the nonwoven fabric may be such a thickness that a sufficient stiffness is imparted to the adhesive bandage when laminating a film on the nonwoven fabric. The nonwoven fabric of this invention can be thinner than that of conventional adhesive bandages. The thickness of the nonwoven fabric is about 20 to 1,000 $\mu$m, preferably 50 to 500 $\mu$m. It is preferable to make the film thin so as to ensure high gas permeability and water vapor permeability.

The film to laminate the fiber fabric in this invention is used to impart water proofing property to the adhesive bandage without much decrease in gas permeability and water vapor permeability of the fiber fabric as well as to ensure a suitable balance of properties when an adhesive bandage is made. The material of the film is required to have a water proofing property and to have sufficient water vapor permeability even after being laminated to a fiber fabric. As such films, known films made of polyurethanes, polyvinyl chloride, polyvinylidene chloride, polyolefines such as polyethylene and polypropylene, polyesters, polyamides and so forth can be used. Polyurethane films and polyester films in particular are preferred among them.

As polyester elastomers, for example, polyester elastomer "Hytrel" (Trade Mark of E. I. DUPONT DENEMOUR AND COMPANY), "Fleclone" (Trade Mark of Nichigo Film Kabushiki Kaisha) and so forth are preferred. Since the laminating film must have a sufficient water proofing property, a film obtained by extrusion molding, blow-molding or the like is desirous. A drawn film may also be used. The laminating film can be also a multilayered film formed by laminating films made of different materials.

If the material of the laminating film has a low water vapor permeability, the film has to be thin in order to have the desirable water vapor permeability. If the material of the laminating film has high water vapor permeability, it can be thick, but has to have suitable stiffness when laminated on the fiber fabric. From this standpoint, the thickness of said film is preferably 50 $\mu$m or less, more preferably 2 to 30 $\mu$m, and even more preferably, 5 to 15 $\mu$m. Since an adjustment of the balance of properties becomes easy by laminating the film on the fiber fabric, it is possible to use a variety of fiber fabrics, especially less stiff and thin ones, and to improve strength and chemical resistance. The method of laminating the film on the fiber fabric is not particularly limited, but the laminating can be carried out by bonding with a bonding agent, heat-fusion or the like. The laminating may be conducted on the fiber fabric either before or after coating the adhesive thereon.

The adhesive used in the adhesive bandage of the present invention is not particularly limited as long as the skin is little irritated and pressure-sensitive adhesion to the skin is provided. Examples of the adhesive include rubbery adhesives, acrylic adhesives, polyurethane adhesives, silicone adhesives and A-B-A type block copolymer type adhesives such as styrene-isoprene-styrene block copolymer type adhesives, etc. The whole adhering surface of the fiber fabric can be coated with such solid adhesives shown above. However, in order to prevent a decrease in water vapor permeability, it is preferred to coat the fiber fabric with a porous adhesive or to pattern-coat with such an adhesive instead of coating the whole surface.

The thickness of the adhesive layer is 25 to 150 $\mu$m, preferably 30 to 60 $\mu$m.

The adhesive layer can be either a solid one or a porous one, but a porous layer is preferred in order to ensure high gas permeability of the adhesive layer. As a method of making the adhesive porous, there is, for example, a method in which a highly water-absorbable polymer is used as a blowing agent, which fully absorbs water, the resulting polymer is dispersed into an adhesive solution, the dispersion is coated, and a moisture is then evaporated to make the adhesive porous. This method is, however, not critical.

Regarding the pattern coat, the adhesive can be coated on the backing sheet by, for example, screen coating or gravure coating. However, these coating methods are not critical.

As a method of coating the adhesive on the backing sheet, there can be used various known methods such as a method in which the fiber fabric is directly coated with the adhesive, a method in which a release paper is coated with the adhesive and then the adhesive is transferred onto the fiber fabric, and the like.

Methods of heat sealing can be that of pressing a subject sheet with a flat face maintaining a predetermined temperature, that of pressing a sheet with, e.g., a rotary press, etc. The method is, however, not critical.

The pattern seal refers to a heat seal method that does not seal the whole surface of the sealing area but leaves unsealed surface portions in the sealing area. The pattern seal of this invention means that sealed surface and unsealed surface makes a pattern such as sea-island distribution (distributing unsealed area over sealed area such as islands in the sea). In the present invention, the sealed portion is the sea and unsealed portion is an island. The ratio of the sea area to the island area is preferably about 10:90 to 50:50. The sealed portion must continue without break, thereby the pad portion is isolated by the sealed area from the surroundings outside. This isolation prevents an invasion of water etc. from the outside. Examples of such pattern seals are shown in (a) to (e) in FIG. 1. However the patterns are not limited to those illustrated in FIG. 1 as long as the above-mentioned conditions are satisfied. The pattern seal provides the sealing area with a higher gas permeability and water vapor permeability than the flat seal, that is referred to herein as "flat seal", since the unsealed surface has higher gas permeability and water vapor permeability than the sealed surface. Further, the pattern seal gives an answer to the problem of the flat seal that the periphery of the adhesive bandage tends to peel of the skin caused by a lowering of adhesive power of the sealed section because the adhesive layer is made thin by pressure and heat applied during heat seal process.

The heat sealing step of the present invention is preferably performed under the condition that the film does not melt but the thermoplastic fiber fabric melts so as to prevent an invasion of water etc. from a cut section of the fiber fabric while maintaining the water proofing property of the film surface. Therefore in order to satisfy such a condition, the melting temperature of the film material is preferably higher than that of the fiber fabric material. Further it is necessary to set the heat seal conditions such as sealing temperature, time, etc. so that the film does not melt but only the fiber fabric melts. For example, in the case of the combination of polyurethane film and hydrogenated styrene-isoprene-styrene block copolymer fiber fabric, the melting temperature of the polyurethane is about 160 to 200° C., and that of the hydrogenated styrene-isoprene-styrene copolymer is about 120° C. And in the case of the combination of polyester film and above fiber fabric, the melting temperature of polyester is about 170 to 210° C. Consequently both cases satisfy the condition that the melting temperature of the film is higher than that of the fiber fabric. Such a combination makes it possible that only the fiber fabric melts when heat seal is performed at about the melting temperature of the film.

The heat seal of the present invention can be performed either on the whole surface of the bandage or on the peripheral portion only. When the whole surface of the bandage is sealed by heating, the gas permeability and water vapor permeability thereof will become lower than if only the periphery thereof is sealed, since the both gas permeability and water vapor permeability of the heat seal area are lower than those of unsealed area. However, the defect can be prevented to some extent by, e.g., selecting a proper sealing pattern and so forth, and in particular there is an advantage that the heat seal can be performed at the same time in a process for laminating a film to a fiber fabric. FIG. 2 illustrates when the bandage of this invention is a dressing for medical treatment. In FIG. 2, the whole surface of the adhesive shown by 4 is pattern-sealed. FIG. 3 shows a side view thereof. FIG. 4 illustrates a side view of a dressing having a pad in the center thereof.

When only the periphery of the bandage is heat-sealed, there is no concern about a lowering of gas permeability or water vapor permeability. In the case of a small bandage such as an adhesive bandage having a pad, there is a problem regarding difficulty of the positioning of heat seal since the sealing area must be made in a constant width all around. This problem can be solved by performing heat sealing and cutting of the bandage at the same time. FIG. 5 shows a front view of an adhesive bandage having a pad of the present invention when only the periphery of the bandage is heat-sealed. In the figure, the hatched portion is heat-sealed. FIG. 6 shows a sectional view thereof.

The adhesive bandage of the present invention may be formed by any method. Examples of such methods include a method in which a long film having a suitable width is wound up to form a sheet adhesive bandage, a method in which a film strip of suitable size is provided, a water-absorbable pad is held on the central portion of the strip, and the adhesive surface is further covered with a release paper to form an individual package of an adhesive bandage, a method in which a strip of suitable size is provided, and its adhesive surface is covered with a release paper without placing a pad to form an individual pack of an adhesive bandage, and so forth.

Fabrics used in the invention have a moisture vapor transmission rate (MVTR) of at least 1000 g/m$^2$/day, preferably at least 2500 g/m$^2$/day, even more preferably, at least about 5000 g/m$^2$/day.

Film used in the invention have an MVTR of at least about 500 g/m$^2$/day, preferably at least about 1500 g/m$^2$/day, even more preferably at least about 2500 g/m$^2$/day.

The fabric/film laminate of the invention has an MVTR of at least about 500 g/m$^2$/day, preferably at least about 1000 g/m$^2$/day, even more preferably at least about 1500 g/m$^2$/day.

The adhesive-coated laminate of the invention has an MVTR of at least about 500 g/m$^2$/day, preferably at least about 750 g/m$^2$/day, even more preferably at least about 1000 g/m$^2$/day.

MVTR values are determined in accordance with Test Method JIS Z 0208 corresponding to ASTM Test Procedure F 1249-90.

This invention will be explained more specifically by referring to the following Examples.

EXAMPLES

Example 1 and Comparative Example 1

A 10 μm-thick polyurethane film was laminated by heat fusion to one surface of a nonwoven fabric which is made by melt-blown spinning of a hydrogenated styrene-isoprene-styrene block copolymer with a styrene content of 27% by weight. The weight of the nonwoven fabric was 50 g/m$^2$. Subsequently, an acrylic adhesive was coated on the opposite surface of the nonwoven fabric such that the thickness of the adhesive layer was 50 μm, and the coated adhesive was dried to thereby obtain an adhesive film for use in making an adhesive bandage. In order to make an adhesive bandage shown in FIG. 5 from this adhesive film, the periphery in 2 mm width of the bandage was heat-sealed, and then the adhesive bandage was made by cutting out in the shape of FIG. 5.

In Example 1, the pattern illustrated in FIG. 1(a) was applied for the heat seal. The length of the diagonal line of the unit square of this pattern was 1 mm. In Comparative Example 1, the bandage was flat-sealed on 2 mm wide peripheral section. A wear test was carried out by using said adhesive bandages as testing samples. The heat seal was performed by a steel roller with a diameter of 120.3 mm having a pattern of FIG. 1(a) on the surface of the roller under the condition of 180° C. in roll surface temperature and 22.2 m/minute in feed velocity.

The wear test was carried out as follows: Test samples of the adhesive bandage were adhered on a finger and an arm of subjects. The subjects engaged in their usual activities, An evaluator evaluated the peeling situation of the adhesive bandage according to the criteria below after 6 hrs and 24 hrs for the finger, and for 24 hrs for the arm. The result was estimated as an average value of the evaluations of all the subjects (1) Wear Test (Finger)
   5 Perfect adhesion
   4 Heat seal is up slightly
   3 One side of a pad off
   2 Both sides of a pad off
   1 Both sides of a pad off and film becomes a wrinkle
   0 Bandage off (2) Wear Test (Arm)
   7 All edges adhering firmly
   6 One or two edges up slightly of heat seal
   5 Heat seal ¼ off
   4 Heat seal ¼ to ½ off
   3 Heat seal ½ to ¾ off
   2 Heat seal all off
   1 Heat seal in addition to flap off
   0 Bandage off The results were shown in Table 1

TABLE 1

| Example No. | | Ex. 1 | C. Ex. 1 |
|---|---|---|---|
| Test items | Test time (hour) | Pattern seal | Flat seal |
| Wear test (finger) | 6 | 3.87 | 3.43 |
|  | 24 | 1.67 | 1.63 |
| Wear test (arm) | 24 | 6.29 | 5.75 |

It was shown that the bandage of Example 1 had a better adhesive property than that of Comparative Example 1 whose whole seal area was sealed, that is, a flat seal.

Example 2, Comparative Example 2

In order to compare the adhesive power of the pattern seal with that of the flat seal, an adhesion test to glass was carried out using the adhesive bandage of Example 1. In Example 2, the pattern seal shown in FIG. 1(a) was used. In Comparative Example 2, a flat seal, the heat seal conditions were the same as Example 1. The testing method of adhesion to glass is as follows:

Adhesion to Glass:

A laminate comprising a film, a nonwoven fabric and an adhesive was cut into a width of 25.4 mm (1 inch) and bonded to a glass plate washed with acetone. A weight load was exerted on the test sample on the glass by one reciprocation with a rubber-coated roller having a weight of 4.5 kg. The pulling rate was set at 300 mm/minute, and the test sample was pulled at an angle of 180° against the adhesive surface. The load weight was recorded when the test pieces were peeled from the glass surface. Test results are shown in Table 2.

TABLE 2

| Example No. | Ex. 2 | C. Ex. 2 |
|---|---|---|
| Seal method | Pattern seal | Flat seal |
| Measurement | 240 | 172 |
| (g/25 mm) | 252 | 183 |
|  | 252 | 183 |
|  | 274 | 194 |
|  | 291 | 229 |
| Average | 262 | 192 |

As shown in Table 2, the adhesive power of the pattern seal is about 36% higher than that of the flat seal.

Example 3

The pattern seal procedure of Example 1 was repeated except that 159 m thickness polyester film (trade name: Fleclone, Nichigo Film Kabushiki Kaisha) was used as the film for the base sheet, and thereby an adhesive bandage was made. This bandage also showed similar practical properties as that of Example 1 and was confirmed to have excellent water resistance and air permeability.

EFFECTS OF THE INVENTION

The adhesive bandage of the present invention shows, by the pattern seal of either the whole surface or the peripheral surface of the bandage, an improved adhesive property to skin without impairing gas permeability and water vapor permeability compared to flat seal bandages wherein the whole seal area is sealed by heating, and may effectively prevent soaking of liquid such as water into an absorbent pad and a wound.

DESCRIPTION OF SYMBOLS

Figure 1A:
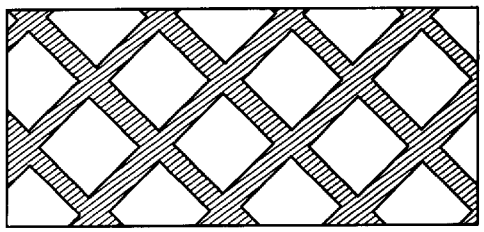
FIGS. 1(a) to (e) show five heat seal patterns used in the present invention.
Figure 1B:
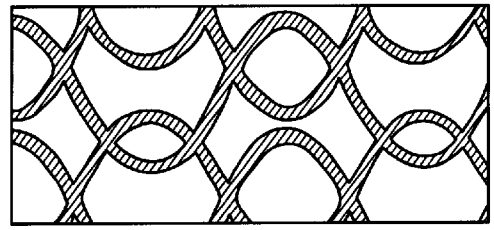
Figure 1C:
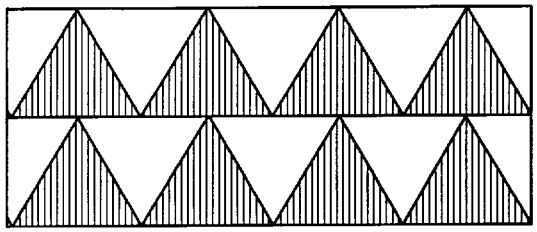
Figure 1D:
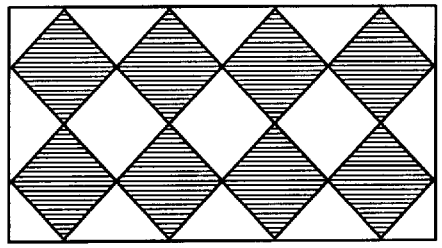
Figure 1E:
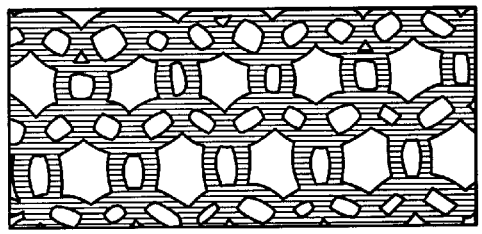
Figure 2:
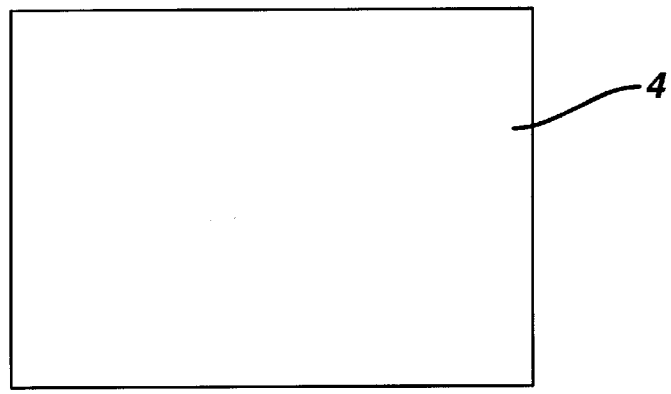
FIG. 2 is a top plan view of a dressing in accordance with the present invention.
Figure 3:
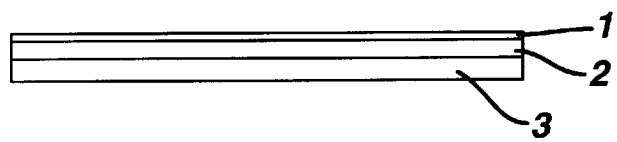
FIG. 3 is a side view of the dressing of FIG. 2.
Figure 4:
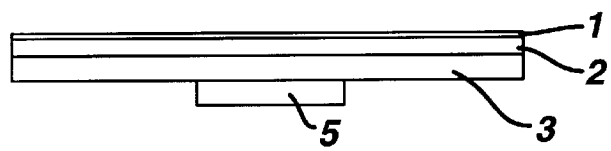
FIG. 4 is a side view of an adhesive bandage according to the present invention, said bandage having a wound-contacting pad in the center thereof.
Figure 5:
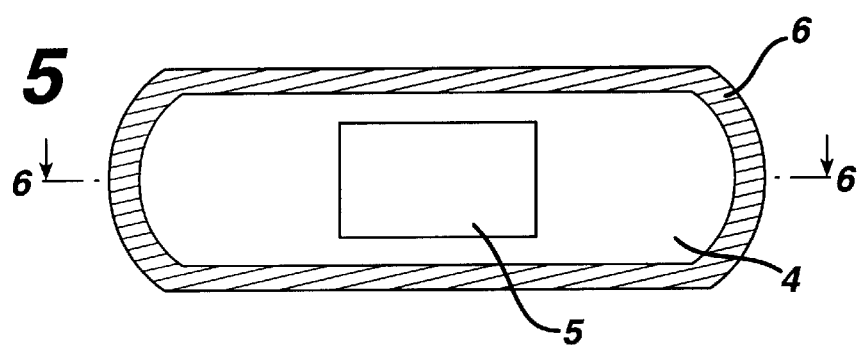
FIG. 5 is a plan view of the adhesive bandage of FIG. 4.
Figure 6:
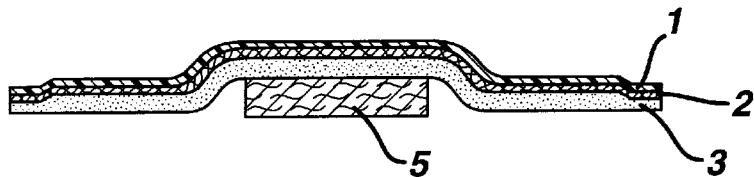
FIG. 6 is a sectional view of the adhesive bandage of FIG. 5.

1 . . . film, 2 . . . fiber fabric, 3' adhesive, 4 adhesive surface, 5 . . . pad, 6 . . . heat seal section.

What is claimed is:

1. A method for making an adhesive-coated sheet material, said method comprising the steps of:
   A. providing a film of polymeric material;
   B. providing a thermoplastic fiber fabric;
   C. laminating said film to said fabric to form a laminated sheet material having a fabric surface and a film surface;
   D. applying a layer of adhesive to said fabric surface of said laminated sheet material; and
   E. heat-sealing at least a portion of said laminated sheet material in a discontinuous pattern.

2. A method according to claim 1 wherein step D is performed before step E.

3. A method according to claim 1 wherein the heat-sealing is performed under conditions such that at least portions of the thermoplastic fiber fabric melt but the film does not melt.

4. A method according to claim 1 wherein only the periphery of the sheet material is heat-sealed in said pattern.

5. A method for making an adhesive bandage, said method comprising the steps of:
   A. providing a film of polymeric material;
   B. providing a thermoplastic fiber fabric
   C. laminating said film to said fabric to form a laminated sheet material having a fabric surface and a film surface;
   D. applying a layer of adhesive to said fabric surface of said laminated sheet material;
   E. heat-sealing at least a portion of said laminated sheet material in a discontinuous pattern; and
   F. securing a wound-contacting pad to the adhesive coating of said laminated sheet material.

6. A method according to claim 5 wherein step D is performed before step E.

7. A method according to claim 5 wherein the heat-sealing is performed under conditions such that at least portions of the thermoplastic fiber fabric melt but the film does not melt.

8. A method according to claim 5 wherein only the periphery of the sheet material is heat-sealed in said pattern.

9. The method of claim 5 further comprising the step of cutting said laminated sheet to form individual bandages.

10. The method of claim 9 wherein said cutting step and said heat-sealing step are performed simultaneously.

11. An adhesive-coated sheet material comprising:
   a. a film of polymeric material;
   b. a thermoplastic fiber fabric, and
   c. an adhesive,
      said film being laminated to said thermoplastic fiber fabric; said laminate having a fabric surface and a film surface;
      said adhesive being applied to said fabric surface of said laminate; and at least a portion of said laminate being heat-sealed in a discontinuous pattern.

12. The adhesive-coated sheet material of claim 11 having a moisture vapor transmission rate of at least about 500 g/m$^2$/day.

13. The adhesive-coated sheet material of claim 11 having a moisture vapor transmission rate of at least about 750 g/m$^2$/day.

14. The adhesive-coated sheet material of claim 11 having a moisture vapor transmission rate of at least about 1000 g/m$^2$/day.

15. An adhesive bandage comprising:
   a. a film of polymeric material;
   b. a thermoplastic fiber fabric;
   c. an adhesive;
   d. a wound-contacting pad;
      said film being laminated to said thermoplastic fiber fabric; said laminate having a fabric surface and a film surface;
      said adhesive being applied to said fabric surface of said laminate; at least a portion of said laminate being heat-sealed in a discontinuous pattern; said pad being secured to said laminate by said adhesive.

16. The bandage of claim 15 wherein said discontinuous heat-sealed pattern comprises sealed portions and unsealed portions, and wherein the area ratio of the sealed portions to the unsealed portions is in the range of about 10:90 to about 50:50.

17. The bandage of claim 15 wherein said discontinuous heat-sealed pattern is only present at the periphery of said bandage.

18. The bandage of claim 17 wherein said discontinuous heat seal pattern completely surrounds the periphery of said bandage.

19. The bandage of claim 15 wherein said film comprises a polymeric material selected from polyurethanes, polyvinyl chloride, polyvinylidene chloride, polyolefins, polyesters, and polyamides; said fiber fabric is selected from woven fabrics and nonwoven fabrics; and said fiber fabric comprises a thermoplastic material selected from styrene-isoprene-styrene block copolymers, hydrogenated styrene-isoprene-styrene block copolymers, polyurethanes, polyesters, polyolefins and mixtures thereof.

20. The bandage of claim 15 wherein said film comprises a polymeric material selected from polyurethane and polyester; said fiber fabric is a nonwoven fabric; and said fiber fabric comprises a thermoplastic material selected from styrene-isoprene-styrene block copolymers, hydrogenated styrene-isoprene-styrene block copolymers and mixtures thereof.

* * * * *